US009814613B2

(12) United States Patent
Griego et al.

(10) Patent No.: US 9,814,613 B2
(45) Date of Patent: *Nov. 14, 2017

(54) RAPID EXCHANGE STENT DELIVERY SYSTEM

(71) Applicant: Boston Scientific Scimed, Inc., Maple Grove, MN (US)

(72) Inventors: John A. Griego, Blackstone, MA (US); David C. Giusti, Somerville, MA (US); Stephen Derosier, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/314,778

(22) Filed: Jun. 25, 2014

(65) Prior Publication Data

US 2014/0309721 A1 Oct. 16, 2014

Related U.S. Application Data

(63) Continuation of application No. 12/879,448, filed on Sep. 10, 2010, now Pat. No. 8,771,335.

(60) Provisional application No. 61/244,301, filed on Sep. 21, 2009.

(51) Int. Cl.
| | | |
|---|---|---|
| *A61F 2/06* | (2013.01) | |
| *A61F 2/966* | (2013.01) | |
| *A61F 2/95* | (2013.01) | |
| *A61F 2/94* | (2013.01) | |
| *A61F 2/04* | (2013.01) | |

(52) U.S. Cl.
CPC .............. *A61F 2/966* (2013.01); *A61F 2/95* (2013.01); *A61F 2/94* (2013.01); *A61F 2002/041* (2013.01); *A61F 2002/9511* (2013.01); *A61F 2002/9517* (2013.01); *A61F 2002/9665* (2013.01)

(58) Field of Classification Search
CPC ...... A61F 2/95; A61F 2/94; A61F 2002/9511; A61F 2/966; A61F 2002/9665; A61F 2002/9517; A61F 2002/041
USPC .................. 623/1.11, 1.12, 1.23, 2.11, 23.7; 606/108, 200; 604/103.04, 164.01, 604/164.12, 166.01, 170.02, 171
See application file for complete search history.

(56) References Cited

U.S. PATENT DOCUMENTS

| | | |
|---|---|---|
| 4,655,771 A | 4/1987 | Wallsten |
| 4,824,435 A | 4/1989 | Giesy et al. |
| 4,848,343 A | 7/1989 | Wallsten et al. |
| 4,913,141 A | 4/1990 | Hillstead |
| 4,913,683 A | 4/1990 | Gregory et al. |
| 4,963,129 A | 10/1990 | Rusch |

(Continued)

FOREIGN PATENT DOCUMENTS

| | | |
|---|---|---|
| EP | 0505686 | 9/1992 |
| JP | 747133 | 2/1995 |

(Continued)

*Primary Examiner* — Jing Ou (57) ABSTRACT

Medical devices and methods for making and using the same. An example medical device may include an elongate tubular member, an endosurgery stent disposed on the outer surface of the tubular member, a push tube slidably disposed along the outer surface of the tubular member, and a push member slidably disposed in a lumen formed in the tubular member. The push member may be coupled to the push tube.

20 Claims, 7 Drawing Sheets

(56) References Cited

U.S. PATENT DOCUMENTS

| | | |
|---|---|---|
| 4,990,151 A | 2/1991 | Wallsten et al. |
| 5,019,085 A | 5/1991 | Hillstead |
| 5,026,377 A | 6/1991 | Burton et al. |
| 5,135,535 A | 8/1992 | Kramer et al. |
| 5,152,749 A | 10/1992 | Giesy et al. |
| 5,217,482 A | 6/1993 | Keith |
| 5,238,004 A | 8/1993 | Sahatjian et al. |
| 5,324,269 A | 6/1994 | Miraki et al. |
| 5,334,185 A | 8/1994 | Giesy et al. |
| 5,360,401 A | 11/1994 | Turnland et al. |
| 5,370,655 A | 12/1994 | Burns et al. |
| 5,372,600 A | 12/1994 | Beyar et al. |
| 5,389,087 A | 2/1995 | Miraki et al. |
| 5,405,378 A | 4/1995 | Strecker |
| 5,458,605 A | 10/1995 | Klemm |
| 5,484,444 A | 1/1996 | Braunschweiler et al. |
| 5,507,768 A | 4/1996 | Lau et al. |
| 5,507,797 A | 4/1996 | Suzuki |
| 5,533,968 A | 7/1996 | Muni et al. |
| 5,571,168 A | 11/1996 | Toro |
| 5,643,278 A | 7/1997 | Wijay et al. |
| 5,690,644 A | 11/1997 | Yurek et al. |
| 5,709,703 A | 1/1998 | Lukic et al. |
| 5,743,874 A | 4/1998 | Fischell et al. |
| 5,782,855 A | 7/1998 | Lau et al. |
| 5,843,028 A | 12/1998 | Weaver et al. |
| 5,921,952 A | 7/1999 | Desmond et al. |
| 5,921,971 A | 7/1999 | Agro et al. |
| 5,980,533 A | 11/1999 | Holman |
| 6,007,522 A | 12/1999 | Agro et al. |
| 6,059,752 A | 5/2000 | Segal |
| 6,077,295 A | 6/2000 | Limon et al. |
| 6,113,607 A | 9/2000 | Lau et al. |
| 6,146,415 A | 11/2000 | Fitz |
| 6,156,062 A | 12/2000 | McGuinness |
| 6,248,100 B1 | 6/2001 | De Toledo et al. |
| 6,264,624 B1 | 7/2001 | Desmond, III et al. |
| 6,309,379 B1 | 10/2001 | Willard et al. |
| 6,380,457 B1 | 4/2002 | Yurek et al. |
| 6,398,799 B2 | 6/2002 | Kramer |
| 6,488,694 B1 | 12/2002 | Lau et al. |
| 6,508,803 B1 | 1/2003 | Horikawa et al. |
| 6,527,789 B1 | 3/2003 | Lau et al. |
| 6,562,024 B2 | 5/2003 | Alvarez de Toledo et al. |
| 6,582,459 B1 | 6/2003 | Lau et al. |
| 6,592,549 B2 | 7/2003 | Gerdts et al. |
| 6,723,071 B2 | 4/2004 | Gerdts et al. |
| 6,764,484 B2 | 7/2004 | Richardson et al. |
| 6,890,317 B2 | 5/2005 | Gerdts et al. |
| 7,001,358 B2 | 2/2006 | Fitzmaurice et al. |
| 7,115,109 B2 | 10/2006 | Gerdts et al. |
| 7,147,655 B2 | 12/2006 | Chermoni |
| 7,468,053 B2 | 12/2008 | Gerdts et al. |
| 7,550,002 B2 | 6/2009 | Goto et al. |
| 2001/0007082 A1 | 7/2001 | Dusbabek et al. |
| 2001/0018574 A1 | 8/2001 | Toledo et al. |
| 2002/0013599 A1 | 1/2002 | Limon et al. |
| 2002/0156496 A1 | 10/2002 | Chermoni |
| 2003/0093106 A1 | 5/2003 | Brady et al. |
| 2003/0109886 A1 | 6/2003 | Keegan et al. |
| 2004/0133263 A1 | 7/2004 | Dusbabek et al. |
| 2004/0199240 A1 | 10/2004 | Dorn |
| 2005/0085891 A1* | 4/2005 | Goto .................. A61F 2/94 623/1.11 |
| 2005/0085892 A1 | 4/2005 | Goto et al. |
| 2005/0177043 A1 | 8/2005 | Windheuser et al. |
| 2006/0276873 A1 | 12/2006 | Sato |
| 2007/0123971 A1* | 5/2007 | Kennedy, II .......... A61F 2/95 623/1.11 |
| 2007/0293929 A1 | 12/2007 | Aoba et al. |
| 2008/0004685 A1 | 1/2008 | Seemann et al. |
| 2009/0105808 A1 | 4/2009 | Gerdts et al. |
| 2009/0143849 A1 | 6/2009 | Ozawa et al. |
| 2009/0254177 A1 | 10/2009 | Yang et al. |
| 2009/0270877 A1 | 10/2009 | Johnson et al. |

FOREIGN PATENT DOCUMENTS

| | | |
|---|---|---|
| WO | 9415549 | 7/1994 |
| WO | 9949808 | 10/1999 |
| WO | 0069498 | 11/2000 |
| WO | 02074378 | 9/2002 |
| WO | 03002033 | 1/2003 |
| WO | 03003944 | 1/2003 |
| WO | 2005117758 | 12/2005 |
| WO | 2006089517 | 8/2006 |
| WO | 2008085714 | 7/2008 |

* cited by examiner

RAPID EXCHANGE STENT DELIVERY SYSTEM

CROSS-REFERENCE TO RELATED APPLICATION

This application is a continuation of U.S. patent application Ser. No. 12/879,448, filed Sep. 10, 2010 which claims priority to U.S. Provisional Patent Application No. 61/244,301, filed on Sep. 21, 2009, the entire disclosure of which is incorporated herein by reference.

FIELD OF THE INVENTION

The present invention pertains to medical devices and methods for manufacturing medical devices. More particularly, the present invention pertains to medical devices for delivering stents to the biliary tract and/or the pancreatic tract.

BACKGROUND

A wide variety of intraluminal medical devices have been developed for medical use, for example, use in the biliary tract. Some of these devices include guidewires, catheters, stents, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices or components thereof. An example medical device may include an elongate tubular member, an endosurgery stent disposed on the outer surface of the tubular member, a push tube slidably disposed along the outer surface of the tubular member, and a push member slidably disposed in a lumen formed in the tubular member. The push member may be coupled to the push tube.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

A wide variety of biliary, endoscopic, and/or endosurgical procedures have been developed for making medical treatments, diagnoses, and images of areas along the biliary tract and/or the pancreatic tract. For the purposes of this disclosure, the "biliary tract" and/or the "pancreatic tract" are understood to include various components of the digestive system and include, for example, the various ducts of the biliary tree between the liver and the duodenum as well as the various ducts between the pancreas and the duodenum. Numerous endoscopic and/or endosurgical devices have been developed for making medical treatments, diagnoses, and images of areas along the biliary and pancreatic tracts. Some of these device and/or procedures include biliary catheters, biliary guidewires, biliary stent delivery systems, and the like. In general, these devices are guided to the biliary and/or pancreatic tract by an endoscope (and/or a duodenoscope) that is disposed in the duodenum. Once positioned, various interventions can be performed depending on the needs of the patient and the type of device utilized.

Figure 1:
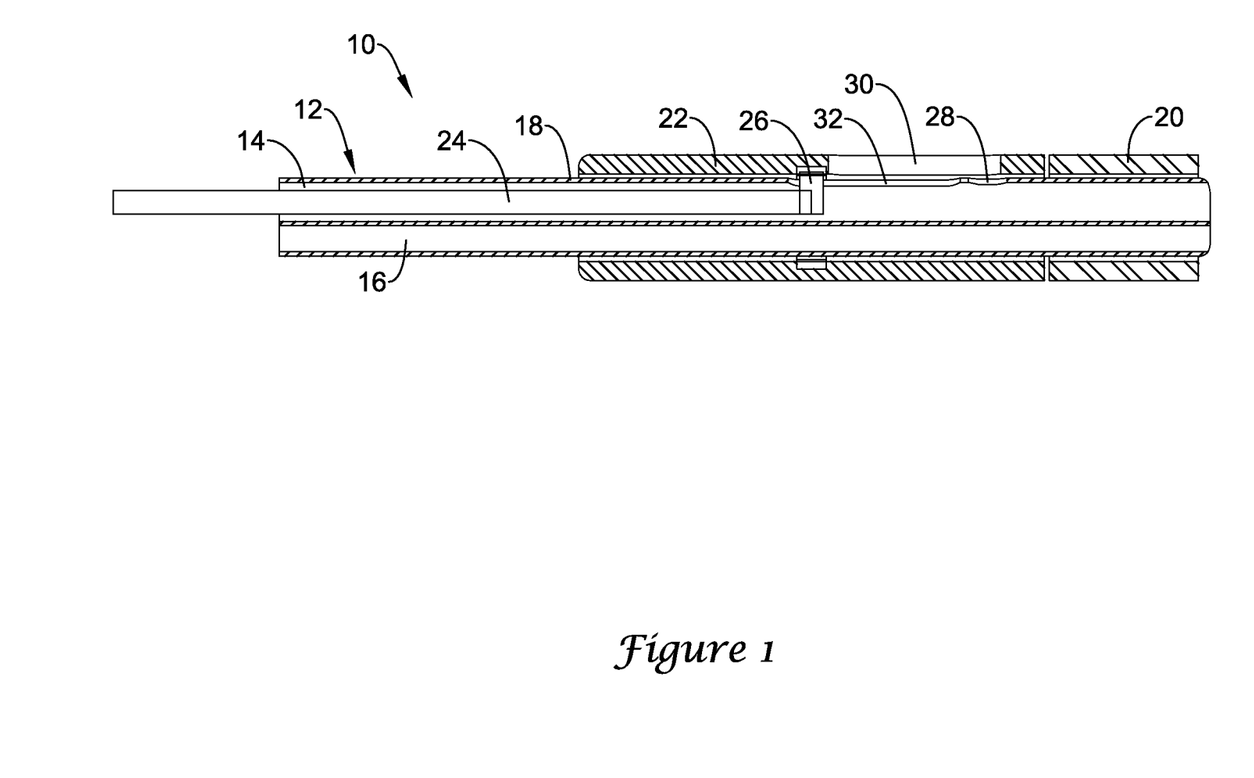
FIG. 1 is a partial cross-sectional side view of an example medical device.

FIG. 1 is a partial cross-sectional side view of an example medical device 10, which takes the form of a prosthesis or stent delivery system. In at least some embodiments, system 10 may be used to delivery a stent along the biliary or pancreatic tract. However, this is not intended to be limiting. For example, system 10 may be used in a wide variety of applications including applications where drainage (e.g., via a stent) is desired. This may include urological applications, gynecological applications, etc.

System 10 may include a catheter or tubular member 12 having a first lumen 14 formed therein, a second lumen 16 formed therein, and an outer surface 18. In some embodiments, tubular member 12 may include additional lumens. Tubular member 12 may include a fluid attachment port at its proximal end (not shown). An endosurgical (i.e., a biliary, pancreatic, etc.) prosthesis or stent 20 may be disposed on outer surface 18. A push tube 22 may also be disposed along outer surface 18. Typically, push tube 22 is disposed proximal of stent 20. A push member 24 may be slidably disposed in lumen 14. Push member 24 is coupled to push tube 22, for example by an attachment member 26. Attachment member 26 may comprise a ring of material that extends around tubular member 18 (and underneath push tube 22) and connects push member 24 to push tube 22.

Figure 2A:
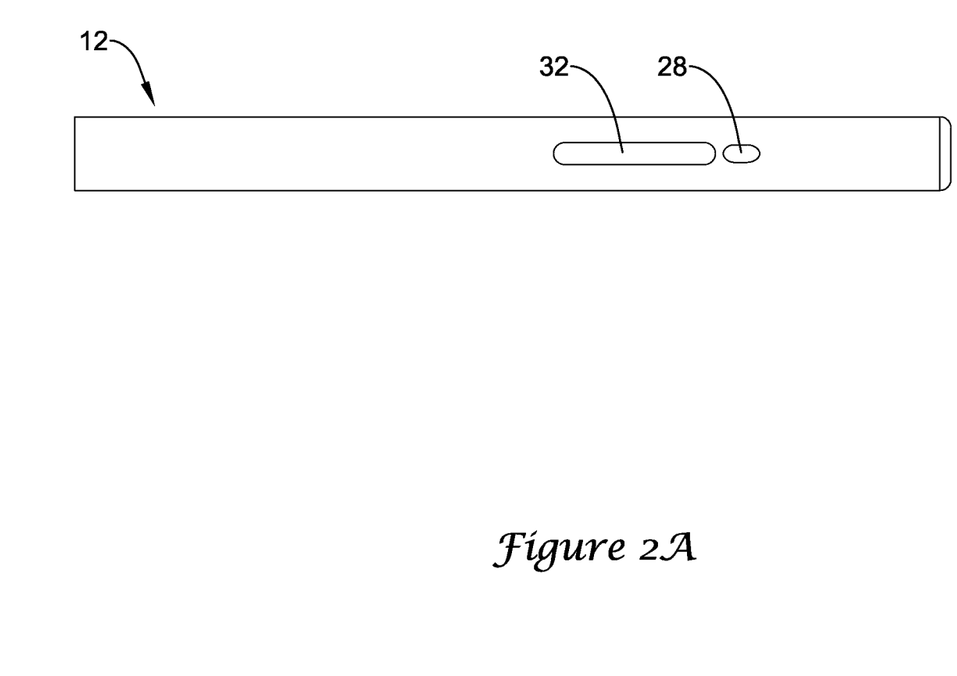
FIG. 2A is a top view of a portion of the device depicted in FIG. 1.

Tubular member 12 may also include a guidewire port 28 (also shown in FIG. 2A). Guidewire port 28 may take the form of an opening in the wall of tubular member 12 that provides access to first lumen 14 for another device such as a guidewire. As such, a guidewire (not shown) may extend along the exterior of system 10, through port 28, and into and through lumen 14 prior to, during, or after an intervention. The position of guidewire port 28 (e.g., near the distal end of tubular member 12) may allow system 10 to function as a "rapid exchange" type of system that is similar to typical rapid exchange systems used in the medical device arts. This feature may be desirable because, for example, it may allow for rapid and easy exchanges of devices or systems (e.g., system 10) over a guidewire as is typical of rapid exchange systems in other art areas.

System 10 may also include one or more seals or sealing members (not shown) arranged at locations that would help reduce and/or prevent fluid leakage along system 10. Such seals may be disposed along tubular member 12, push tube 22, push member 24, junctions between these and/or other structures, and/or any other suitable location.

Figure 2B:
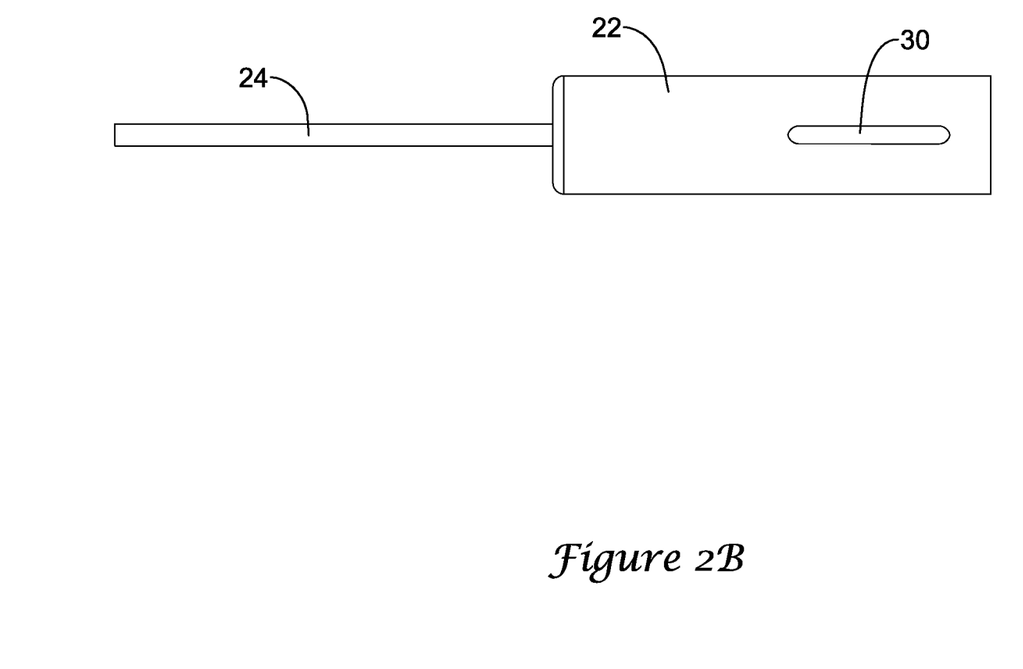
FIG. 2B is a top view of another portion of the device depicted in FIG. 1.

Turning now to FIG. 2A, which illustrates shaft 12 with push tube 22 removed, it can be seen that tubular member 12 may include a guidewire port clearance slot or attachment member slot 32 that is generally disposed adjacent to guidewire port 28. Attachment member clearance slot 32 generally provides an opening in the wall of tubular member 12 so that push tube 22 can slide along outer surface 18 while being connected with push member 24. Slot 32 may allow, for example, a portion of push member 24, attachment member 26, or another intermediate member disposed between push tube 22 and push member 24 to slide therein during deployment of stent 20. Similarly, push tube 22 may include a guidewire port slot 30 that may allow push tube 22 to slide along a guidewire (e.g., a guidewire disposed in lumen 14 and/or through port 28) during deployment of stent 20 without altering the position or configuration of the guidewire as shown in FIG. 2B.

Figure 3:
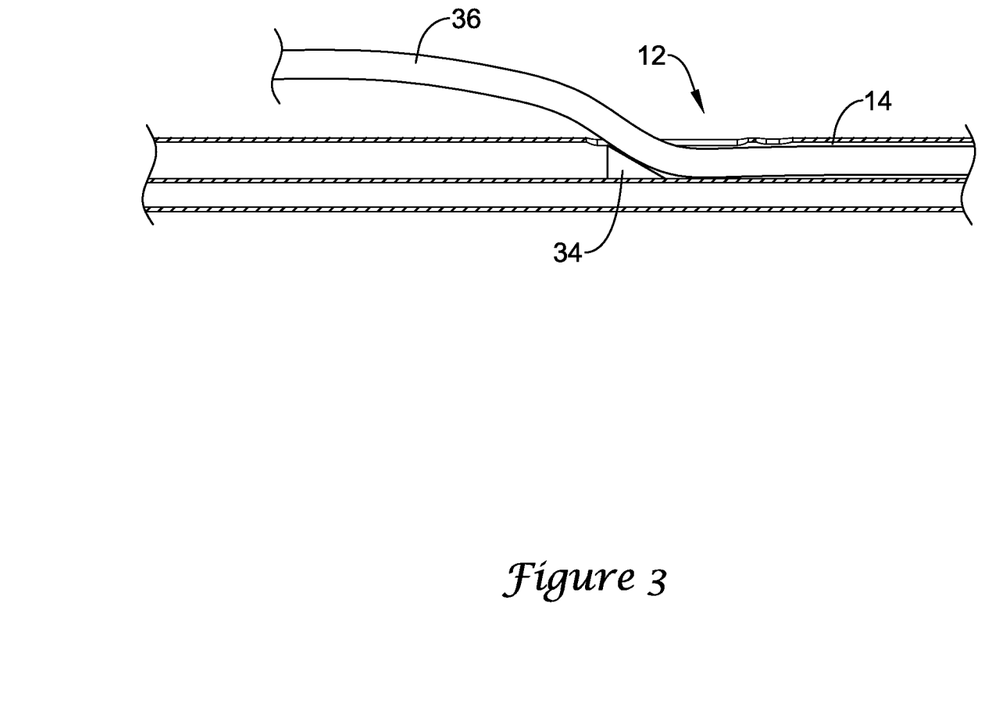
FIG. 3 is a partially cut-away view of a portion of an example medical device showing a guidewire ramp formed therein.

In at least some embodiments, a guidewire ramp 34 may be disposed in first lumen 14 as illustrated in FIG. 3. Ramp 34 may be formed by skiving tubular member 12, by disposing a structure in lumen 14 that forms ramp 34, or in any other suitable manner. In FIG. 3, push tube 22 is removed so that ramp 34 can be more clearly seen and for simplicity. Guidewire ramp 34 may function by directing a guidewire 36 from first lumen 14, through guidewire port 28, and through guidewire port slot 30 to a position along the exterior of system 10. In at least some embodiments, guidewire ramp 34 may substantially fill a portion of lumen 14. This feature may be desirable for a number of reasons. For example, filling lumen 14 may help to ensure that guidewire 36 properly finds its way out through port 28 without interfering with push member 24 or any other structure. In addition, filling lumen 14 may also create a physical barrier that prevents push member 24 from translating too far distally during an intervention. Thus, ramp 34 may also function as a distal stop. It can be appreciated that when ramp 34 fills lumen 14, ramp 34 may divide lumen 14 into two sections or "sub-lumens" so that tubular member 12 can be thought to have a total of three lumens formed therein.

Second lumen 16 is generally positioned parallel to first lumen 14 and it may be distinct and independent from first lumen 14. In other words, along tubular member 12 there may be no openings or passageways that extend between lumens 14/16 such that no fluid communication occurs between lumens 14/16. As such, second lumen 16 may comprise an injection lumen and/or an aspiration lumen that can be used independently from first lumen 14. Thus, during a stent placement intervention, first lumen 14 can be used as a place for push member 24 to slide and for guidewire placement and second lumen 16 can be used independently for the injection of diagnostic and/or treatment materials, the aspiration of materials, or any other suitable use. For example, second lumen 16 can be used for the injection of contrast material in order to improve the visualization of system 10 during an intervention. In addition or in the alternative, second lumen 16 (and/or other lumens that may be formed in system 10) may be utilized to advance other devices to a target site including, for example, sphincterotomes, needles, baskets, and the like, or any other suitable device.

In at least some embodiments, tubular member 12 may have a hub assembly (e.g., a Y type hub assembly) coupled to or otherwise attached at its proximal end (not shown). The hub assembly may allow for other ancillary devices to be secured to tubular member 12 and, for example, gain access to lumen 16. To facilitate such securing of ancillary devices, the hub assembly may include a connector such as a standard luer lock connector or any other suitable connector. Additionally, the hub assembly may include a locking mechanism for securing the position of guidewire 36. This may allow guidewire 36 to be held stationary, for example, when push member 24 is advanced, retracted, or at essentially any intermediate position.

In use, system 10 may be advanced through an endoscope or duodenoscope (not shown) to a suitable location near a target site. Once positioned, push member 24 can be urged distally, thereby causing push tube 22 to slide distally along outer surface 18 of tubular member 12 and push stent 20 off of outer surface 18, thereby deploying stent 20. Alternatively, tubular member 12 can be proximally retracted while holding push member 24 (and, therefore, push tube 22) substantially stationary, thereby allowing stent 20 to emerge off from tubular member 12. In still alternative embodiments, a combination of these two strategies can be utilized. After deploying stent 20, system 10 can be retracted from the endoscope. Some additional details regarding this and other uses, including variations and/or additions to this use, are described in more detail below.

The movement of push member 24 and/or other structures of system 10 may be facilitated through the use of a handle (not shown) that may be attached to or formed at the proximal end of system 10. The handle, which may be a soft coated handle that includes a thermoplastic elastomer (TPE), a thermoplastic polyolefin (TPO), or the like, may include one or more structures (e.g., dials, sliders, wheels, buttons, etc.) that may allow the user to easily manipulate the various structures of system 10. In some embodiments, a ratchet or ratcheting system may also be associated with the handle so that the user can manipulate the various components of system 10 in a controlled, ratchet-like manner.

Manufacturing system 10 may include a variety of method steps. At least some of these steps are determined by the materials selected for the various components of system 10. For example, when tubular member 12, push member 24, and/or other components of system 10 are made from an extrudable polymer, the manufacturing of tubular member 12 may include extrusion of the polymer to form the appropriate structures. Once the extrusion is completed, the various structures can be coupled together in any suitable manner to complete the manufacture of system 10. Numerous other methods are contemplated including, for example, molding (including injection molding), casting, and the like.

Variations on these methods are also contemplated when these or other materials are utilized including those materials disclosed herein. In general, system 10 may include a variety of materials including metals, metal alloys, polymers (some examples of which are disclosed below), metal-polymer composites, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

As alluded to above, within the family of commercially available nickel-titanium or nitinol alloys is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear or a somewhat but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2 to about 5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to about 0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol, can be used to achieve desired properties.

In at least some embodiments, portions or all of system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of system 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of system 10 to achieve the same result. In addition, portions or all of system 10 may include markings that may be used to gage the position, for example, of tubular member 12, push tube 22, push member 24, etc. within the anatomy.

In some embodiments, a degree of MRI compatibility is imparted into system 10. For example, to enhance compatibility with Magnetic Resonance Imaging (MRI) machines, it may be desirable to make portions or all of system 10 in a manner that would impart a degree of MRI compatibility. For example, portions or all of system 10 may be made of a material that does not substantially distort the image and create substantial artifacts (artifacts are gaps in the image). Certain ferromagnetic materials, for example, may not be suitable because they may create artifacts in an MRI image. Portions or all of system 10 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be utilized in the manufacturing of system 10 and/or the various components thereof may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, poly(L-lactide) (PLLA), poly(D,L-lactide) (PLA), polyglycolide (PGA), poly(L-lactide-co-D, L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), polyphosphate ester), poly(amino acid), polyacrylate, polyacrylamid, poly(hydroxyethyl methacrylate), polyurethane, polysiloxane and their copolymers, or mixtures or combinations thereof.

Figure 4:
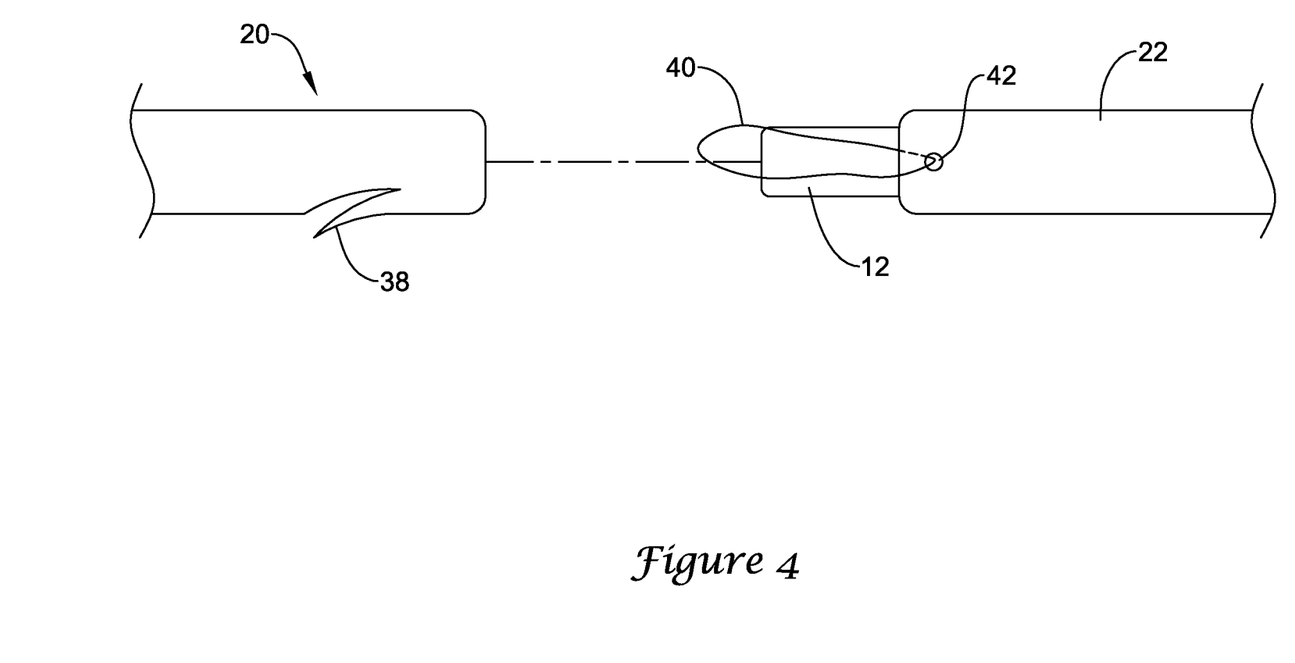
FIG. 4 is an exploded perspective view of an example medical device and an endosurgery stent.
Figure 5:
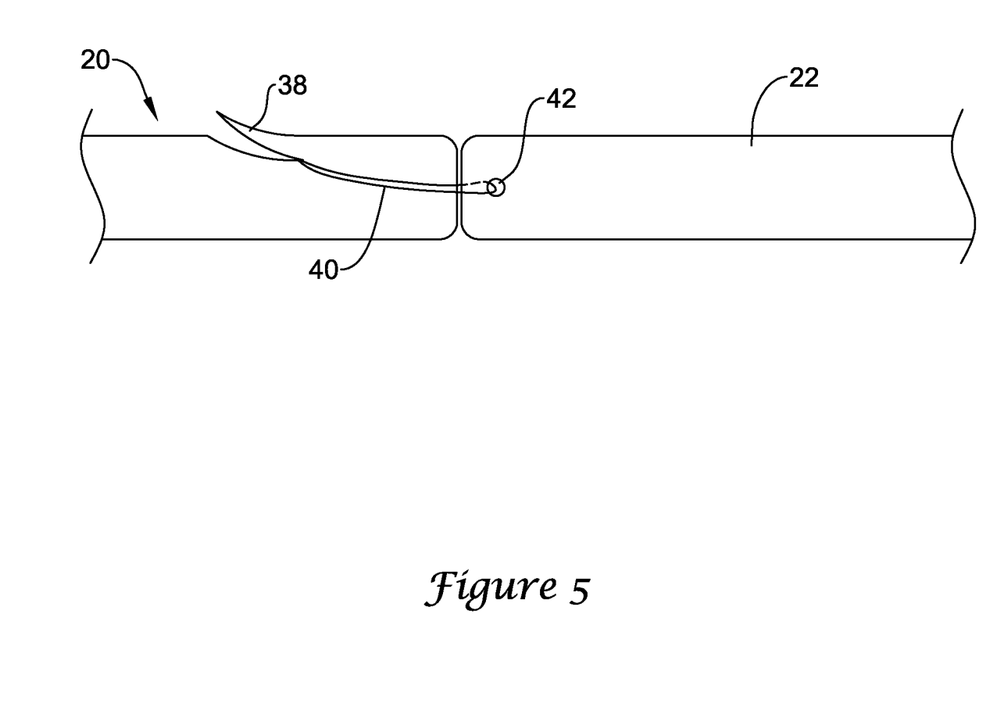
FIG. 5 is a perspective view of an example medical device with an endosurgery stent coupled thereto.
Figure 6:
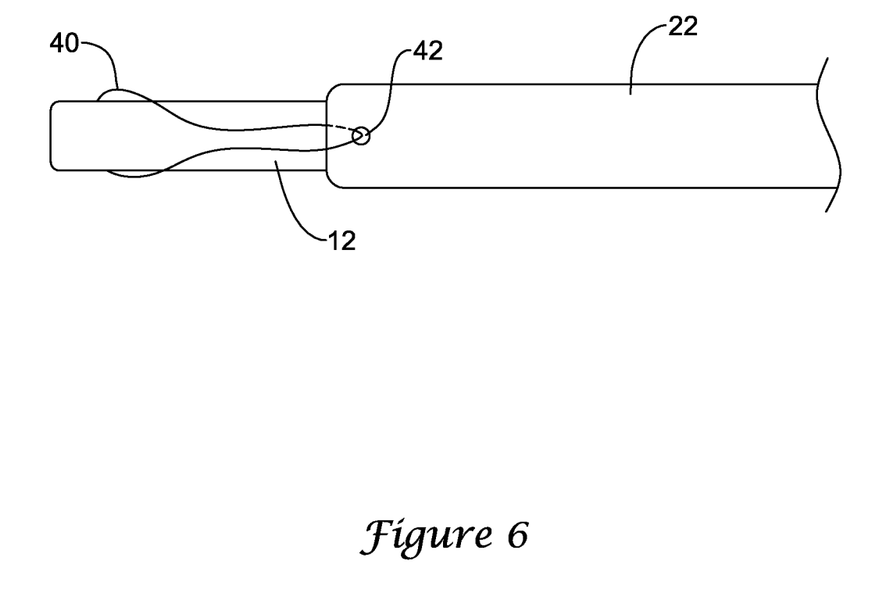
FIG. 6 is a perspective view depicting the arrangement of a suture member relative to a tubular member.

FIGS. 4-6 illustrate some additional features of system 10 as well as depict how stent 20 may be coupled to and held on tubular member 12. Stent 20, as depicted in FIG. 4, may comprise a polymeric tube or cylinder with a central lumen (so that stent 20 can be fitted over tubular member 12) and one or more slots formed therein that form a define one or more flaps 38 along the exterior thereof. For example, stent 20 may include a proximal flap 38 (as shown) and a distal flap (not shown) that is similar to proximal flap 38. Flaps 38 may provide stent 20 with a number of desirable features. For example, flaps 38 (e.g., a distal flap) can be disposed within the bile duct or pancreas duct and prevent migration of stent 20 out of the duct during an intervention. Another flap (e.g., a proximal flap) may remain outside of the duct, for example in the duodenum, and prevent migration of stent 20 into the duct during the intervention. Prior to delivery, flaps 38 may be held flat by a suitable sheath of material so that system 10 can be loaded into an endoscope. During delivery of stent 20, flaps 38 may be held flat within the endoscope. After emerging from the endoscope, flaps 38 may resume their shape (e.g., as illustrated in FIG. 4).

It can be appreciated that stent 20, which takes the form of an endosurgical (e.g., biliary and/or pancreatic) stent 20 differs from intravascular stents. For example, stent 20 is typically made from a polymeric material and is typically delivered in a "normal" or non-compressed state. Conversely, intravascular stents are typically delivered in a compressed stated (e.g., compressed onto a catheter and/or a balloon) and then expanded by a balloon and/or by virtue of their material composition (e.g., when made from self-expanding shape memory materials such as nitinol). Other distinctions between stent 20 and intravascular stents can be appreciated by those with ordinary skill in the art.

In order to improve the attachment or coupling between stent 20 and tubular member 12 during delivery, a suture member 40 may be used. Suture member 40 may be any type of suture or suturing structure and/or any other suitable structure that may include a loop. Suture member 40 may be strung through one or more suture openings 42 on push tube 22 and formed into a loop. The free end of suture member 40 (e.g., the loop) may be disposed in the opening of stent 20 that is defined at flap 38 as illustrated in FIG. 5. Tubular member 12 may enter the lumen of stent 20 and pass through the loop of suture member 40. This arrangement is depicted in FIG. 6 in the absence of stent 20. This arrangement will essentially "trap" stent 20 between tubular member 12 and push tube 22. To deploy stent 20, push tube 24 may be distally advanced and/or tubular member 12 may be proximally withdrawn so that tubular member 12 withdraws out from the loop of suture member 40, thereby "freeing" stent 20 from suture member 40.

The arrangement of the various structures of system 10 may vary. In some embodiments, system 10 may include any of the structures or utilize any of the arrangements of structures that are disclosed in U.S. Pat. Nos. 5,334,185 and 5,152,749, the entire disclosures of which are herein incorporated by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. A stent delivery system, comprising:
an elongate tubular member having a first lumen formed therein and a longitudinal slot;
a push tube disposed along an outer surface of the elongate tubular member, wherein the push tube has a first attachment point;
a stent, wherein the stent is disposed along the outer surface of the elongate tubular member; and
a push member disposed within the first lumen of the elongate tubular member, wherein the push member has an attachment member and wherein the attachment member extends through the longitudinal slot and is coupled to the push tube at the first attachment point such that the push tube is slidable along an outer surface of the elongate tubular member.

2. The stent delivery system of claim 1, wherein the push member is capable of sliding longitudinally along the elongate tubular member.

3. The stent delivery system of claim 1, wherein the push tube further comprises a guidewire slot, wherein the guidewire slot substantially aligns with the longitudinal slot.

4. The stent delivery system of claim 1, wherein the push tube further comprises an inner surface including a recessed area.

5. The stent delivery system of claim 4, wherein the inner surface includes an attachment point.

6. The stent delivery system of claim 4, wherein the attachment member includes a ring, and wherein the ring is capable of being inserted into the recessed area.

7. The stent delivery system of claim 1, wherein the elongate tubular member includes a second lumen, wherein the second lumen is disposed adjacent the first lumen.

8. The stent delivery system of claim 1, wherein the elongate tubular member further comprises a guidewire opening, and wherein the guidewire opening is longitudinally aligned with the longitudinal slot.

9. The stent delivery system of claim 8, wherein the guidewire opening is capable of allowing a guidewire to extend through both the guidewire opening and the longitudinal slot.

10. The stent delivery system of claim 1, wherein the elongate tubular member includes a guidewire ramp.

11. The stent delivery system of claim 10, wherein the guidewire ramp is capable of directing a guidewire disposed inside the elongate tubular member through the longitudinal slot, through a guidewire slot formed in the push tube, or both.

12. The stent delivery system of claim 1, wherein the stent delivery system includes one or more suture loops and one or more stent retainment members, wherein the one or more suture loops releasably engage the one or more stent retainment members.

13. A stent delivery system, comprising:
   a first tube having a first lumen, a second lumen, and a first opening formed therein;
   a second tube disposed along an outer surface of the first tube, the second tube having a second opening formed therein;
   a stent disposed along the outer surface of the first tube;
   wherein the first opening is aligned with the second opening;
   a support member slidably disposed inside the first lumen;
   a connector extending through the first opening; wherein the connector is slidable within the first opening; and
   wherein the connector is coupled to the support member and to the second tube.

14. The stent delivery system of claim 13, wherein the second tube further includes an attachment portion.

15. The stent delivery system of claim 13, wherein the first tube further comprises a guidewire opening formed therein, and wherein the guidewire opening is substantially aligned with the first opening and the second opening.

16. The stent delivery system of claim 13, wherein the connector further comprises a ring.

17. The stent delivery system of claim 13, wherein the first tube includes a guidewire ramp.

18. The stent delivery system of claim 13, further comprising one or more suture members.

19. The stent delivery system of claim 18, wherein at least one suture member releasably secures the stent to the outer surface of the first tube.

20. A stent delivery system, comprising:
   a first tube having a first lumen, an opening, an outer surface and a stent retention portion;
   a stent slidably disposed on the stent retention portion of the first tube;
   a second tube slidably disposed radially over the outer surface of the first tube proximal a proximal end of the stent;
   wherein the second tube is capable of advancing in a distal direction;
   wherein advancement of the second tube in a distal direction causes a distal end of the second tube to contact the proximal end of the stent;
   an actuating member slidably disposed in the first lumen and coupled to the first tube;
   wherein the actuating member is capable of advancement in a distal direction; and
   wherein advancement of the actuating member in a distal direction causes the second tube to advance in the distal direction.

* * * * *